(12) United States Patent
Chang et al.

(10) Patent No.: US 6,532,067 B1
(45) Date of Patent: Mar. 11, 2003

(54) AEROSOL FLUORESCENCE SPECTRUM ANALYZER FOR RAPID MEASUREMENT OF SINGLE AIRBORNE PARTICLES

(75) Inventors: Richard K. Chang, New Haven, CT (US); Young-Le Pan, New Haven, CT (US); Ronald G. Pinnick, Columbia, MD (US); Steven C. Hill, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/579,707

(22) Filed: May 25, 2000

Related U.S. Application Data

(60) Provisional application No. 60/147,794, filed on Aug. 9, 1999.

(51) Int. Cl.[7] ............................................. G01N 21/64
(52) U.S. Cl. ..................... 356/318; 250/461.1
(58) Field of Search ......................... 356/73, 317, 318, 356/336; 250/458.1, 459.1, 461.1, 461.2

(56) References Cited

U.S. PATENT DOCUMENTS

| | | | | |
|---|---|---|---|---|
| 5,681,752 A | * | 10/1997 | Prather | 250/281 |
| 5,701,012 A | * | 12/1997 | Ho | 250/461.2 |
| 5,895,922 A | * | 4/1999 | Ho | 250/492.1 |
| 5,999,250 A | * | 12/1999 | Hairston et al. | 250/461.2 |

* cited by examiner

*Primary Examiner*—F. L. Evans
(74) *Attorney, Agent, or Firm*—Mark Kelly; William V. Adams

(57) ABSTRACT

A method for fluorescence probing of particles flowing in a fluid includes defining a trigger volume in the fluid by intersecting a plurality of substantially orthogonally aimed trigger laser beams, each of a different wavelength, detecting light scattered from the vicinity of the trigger volume by a plurality of particle detectors each sensitive to a wavelength corresponding to the wavelength of a trigger laser beam, probing the particles with a pulsed laser triggered by the particle detectors, collecting fluorescence emitted from the particle in a detection volume and focusing it in a detection region, detecting the fluorescence focused in the detection region. The invention also includes devices for carrying out the foregoing method.

18 Claims, 3 Drawing Sheets

AEROSOL FLUORESCENCE SPECTRUM ANALYZER FOR RAPID MEASUREMENT OF SINGLE AIRBORNE PARTICLES

CLAIM TO PRIORITY

Applicants claim domestic priority under 35 U.S.C. §119 (e) based on provisional application Ser. No. 60/147,794 having a filing date accorded to it of Aug. 9, 1999.

FIELD OF INVENTION

This invention pertains generally to fluorescence spectrum analyzers and more specifically to fluorescence spectrum analyzers for measurement of bioaerosols or other single airborne particles.

BACKGROUND OF INVENTION

Bioaerosols, i.e., airborne microorganisms, have both natural and anthropogenic sources. They are found in the workplace and in homes. High concentrations may occur in or around buildings with defective air handling or air-conditioning systems, in houses with domestic animals, in manufacturing operations in which metalworking fluids are used, in dairy or other operations in which animals are confined, in sites of sludge application, in recycling or composting plants, and in sewage plants. Unlike most common atmospheric aerosols, airborne microorganisms can cause diseases, and, along with other biological (e.g., dust mite allergens) and non-biological (e.g., diesel exhaust particles) aerosols can cause allergies and respiratory problems. Bioaerosols are also feared as potential biowarfare and terrorists agents.

Improved methods for measuring aerosols, particularly bioaerosols, are needed. Presently, methods that measure aerosol size distributions in real time provide almost no information about particle types and are not able to identify specific microorganisms. For most allergens, toxins, or microorganisms, culturing the sample or the use of specific protein or nucleic acid recognition molecules is required.

There are presently several methods under development which, while not able to specifically identify bioaerosol particles, can run continuously and give an indication of the presence of biological aerosols. Several fluorescence particle counter devices that measure the elastic scattering and undispersed fluorescence of single aerosol particles as they are drawn through an optical cell have been developed (see Pinnick et al, 1995; Hairston et al, 1997; Seaver et al, 1999 references, below). These devices have shown promise for differentiating between biological and at least some nonbiological aerosols. However, they hold limited promise for classifying biological aerosols. Rather primitive techniques for measuring the fluorescence spectra of single aerosol particles have also been demonstrated (see Nachman et al, 1996; Chen et al, 1996; and Pinnick et al, 1998 references above). However, these techniques are not capable of measuring single particle spectra with a sufficient signal-to-noise ratio to be useful for classifying micrometer-sized biological particles.

In monitoring harmful bioaerosols a rapid response may be necessary in situations where it would be impractical to continuously run a sampler/identifier (a real time monitor might also suggest when to sample for specific harmful bioaerosols). Furthermore, recognition molecules are not always available for all particle types of interest (new bioaerosols may appear). In addition, some studies of bioaerosol dynamics and reactions (evaporation, growth, agglomeration, mixing, etc.) require real-time monitoring capability. Finally, in searching for or studying intermittent sources of bioaerosols, a rapid response may be advantageous. Despite the significant advancement in capabilities of the techniques referred to above, none of these methods are capable of measuring the fluorescence spectra of single micrometer-sized biological particles with a sufficient signal-to-noise ratio to classify them.

Building a point detector that exploits the intrinsic fluorescence of bioaerosol particles for their detection and classification is technically challenging for several reasons. First, particles of interest may exist as a small concentration in a dominant background. Average fluorescence spectra accumulated for a population of aerosol particles may yield little or no information about the few particles of interest (i.e., single-particle spectra are required). Second, fluorescence signals are weak because single particles contain only a few picograms of material, and only a small fraction of the mass of biological particles consists of fluorophors. Third, particles are generally dispersed nonuniformly in the air (their concentration fluctuations follow the Kolmogorov spectrum of atmospheric turbulence), and they must be detected at random times as they are carried rapidly by a stream of air through an optical cell. Fourth, an optimal detector should excite particles in the ultraviolet where most biological particles (and biological molecules) fluoresce efficiently. Ultraviolet laser sources are costly and have relatively low energy output. Fifth, bioaerosols of interest, including individual particles in bioaerosols, may be complex mixtures. Fluorescence from various components of the mixture may limit the usefulness of classification schemes. If fluorescence emission bands were narrow and the number of possible materials in a single particle were small, then it would likely be possible to solve the inverse problem and determine the materials that contributed to the spectrum. However, the intrinsic fluorescence bands from biological materials tend to be spectrally wide; the primary fluorophors in the majority of bioaerosols fall into only a few broad categories (e.g., the aromatic amino acids, tryptophan, tyrosine, and phenylalanine; nicotinamide adenine dinucleotide compounds (NADH); flavins; and chlorophylls); and the number of possible materials is very large. The differences between spectra of bacteria appear to depend on preparation methods (growth media, type and extent of washing of the samples, etc.) more than they depend on intrinsic variations between well-purified bacteria. Therefore, it will not be possible, except with severely restricted classes of bioaerosols, to identify specific bioaerosols based solely on their fluorescence spectra and their size (as determined from elastic scattering). The extent to which it will be possible to characterize naturally occurring and anthropogenically produced bioaerosols (e.g., group them into a few or even a few tens of categories) is yet unknown, however, it is expected that devices according to the invention described herein will provide highly reliable and rapid bioaerosol fluorescence spectra and particle size.

OBJECTS AND SUMMARY OF INVENTION

Accordingly, it is an object of the present invention to provide a device that is capable of reliable and rapid fluorescence spectrum detection, particle sizing, analysis, and classification of biological aerosols. These and other objects are achieved, at least in part, by an Aerosol Fluorescence Spectrum Analyzer (AFSA) that includes an optical element which transfers light from a particle detection volume in a first focal plane to second focal plane; an aerodynamic flow system to move particles to and through the detection volume; a first trigger laser emitting a beam of wavelength $\lambda_1$ and focused in a trigger region through which the particles flow on their way to the detection region; a second trigger laser emitting a beam of wavelength $\lambda_2$ aimed in a direction approximately orthogonal to the direction of the first particle detecting beam and focused on the trigger region; a first wavelength-selective photodetector sensitive to light scattered from the trigger region and emitting an output signal in response to light of wavelength $\lambda_1$ in a predetermined intensity range; a second a wavelength-selective photodetector sensitive to light scattered from the trigger region and emitting an output signal in response to light of wavelength $\lambda_2$ in a predetermined intensity range; a pulsed probe laser which emits a pulse of light centered on the particle detection volume triggered by the logically ANDed output signals of the first and second wavelength-selective photodetectors to emit a pulse of light substantially in the first focal plane but downstream from the particle detection volume; a spectral dispersing element positioned in the second focal plane; and a photosensor connected optically to the spectral dispersing element, triggered by the logically ANDed outputs of the first and second wavelength-selective photodetectors.

Various other features, objects, and advantages of the present invention and the manner in which they are achieved will become apparent after reading the following detailed description, drawings and claims.

DRAWING FIGURES

Figure 1A:
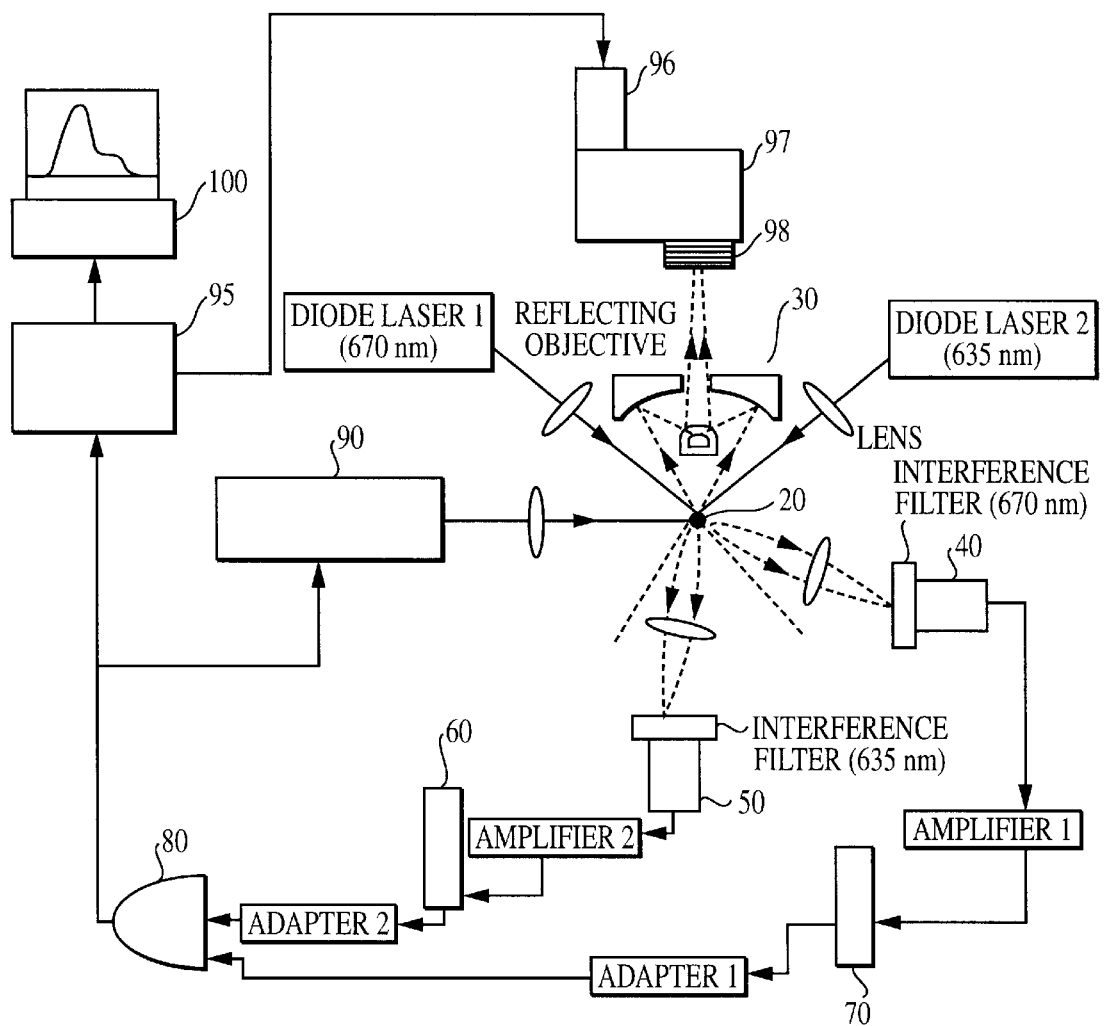

FIG. 1a. shows a top view schematic diagram of an aerosol fluorescence spectrum analyzer according to the present invention.

Figure 1B:
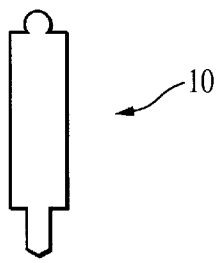

FIG. 1b. shows an ink jet aerosol generator directing a stream of air on FIG. 1a.

Figure 2:
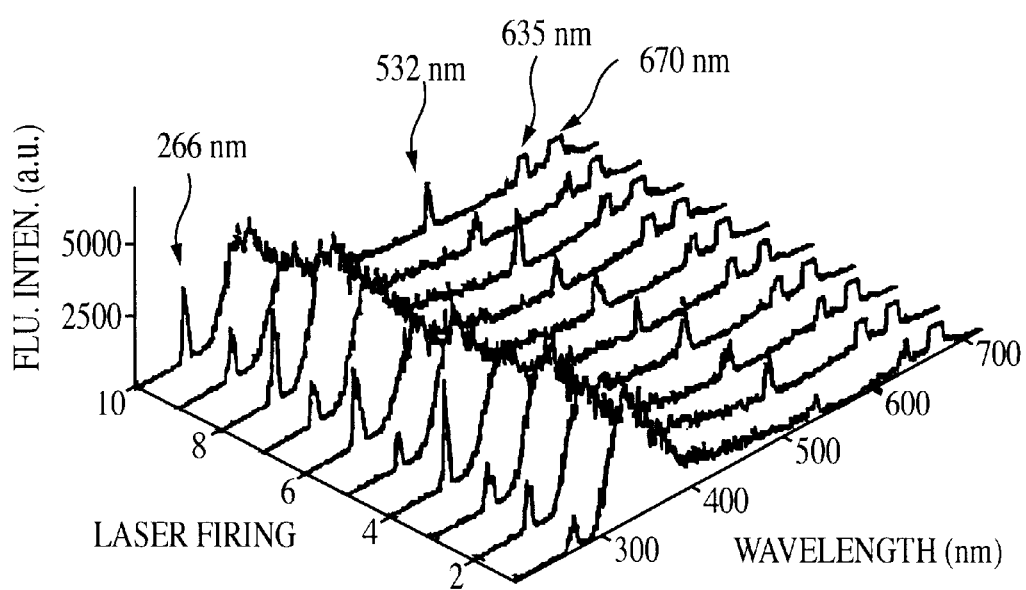

FIG. 2. shows a graph of 10 consecutive single-particle 266-nm-excited fluorescence spectra of nominal 4 micron diameter particles composed of E. coli bacteria.

Figure 3A:
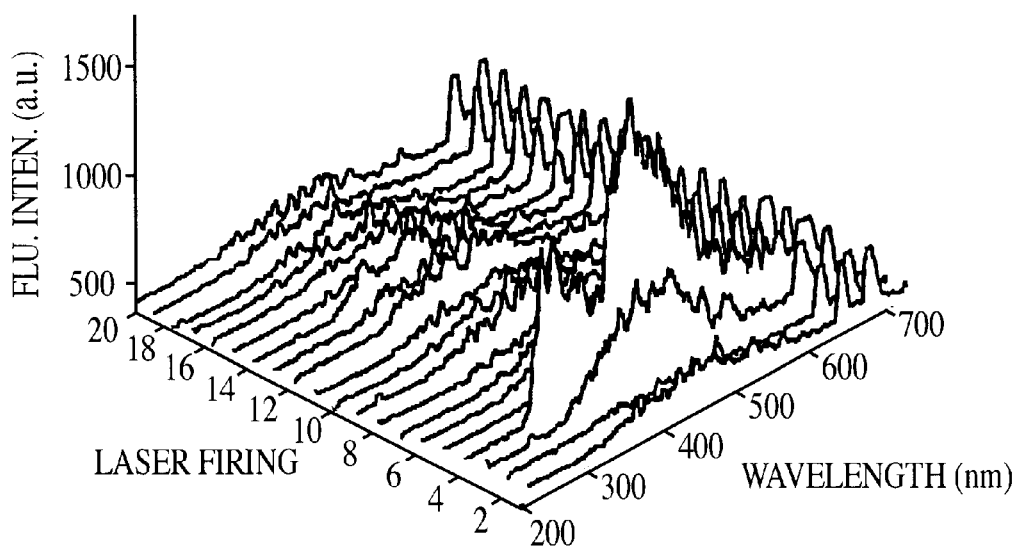
Figure 3B:
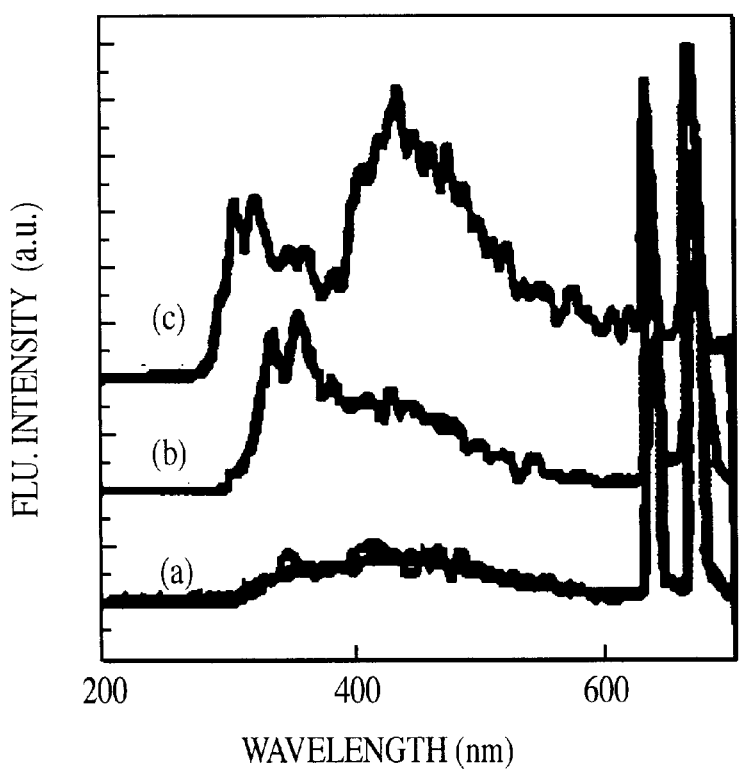

FIGS. 3a and 3b show a graph of 20 consecutive single-particle 266-nm-excited fluorescence spectra of aerosolized particles generated from chicken house dust of nominal average diameter of 3 microns.

DETAILED DESCRIPTION

An aerosol fluorescence spectrum analyzer according to the present invention (AFSA) has distinct advantages. It will detect most bioaerosols in real time without using reagents, and be able to detect minority types of particles even when they are mixed as a tiny concentration with nonbiological particles. AFSA's according to the present invention will be useful for classifying atmospheric bioaerosols into some as yet unknown set of classes, even for particles as small as 2 micrometers in diameter.

Aerosol Fluorescence Spectrum Analyzers (AFSAs) rapidly measure the fluorescence spectra of single micrometer-sized biological particles (and other particles) in real time. The AFSA can measure single particle spectra with good signal-to-noise making it useful for classifying biological particles. Measurements that the AFSA is capable of making are technically challenging for several reasons. First, fluorescence signals are small: the AFSA detects fluorescence from single particles containing only a few picograms of material, and only a small fraction of the mass of biological particles consists of fluorophors. Second, since aerosol particles are mixed randomly in the air, the AFSA measures spectra of particles at random times as they are directed rapidly through an optical cell. Third, the AFSA excites fluorescence in the ultraviolet where most biological particles (and biological molecules) fluoresce efficiently.

Referring now to FIG. 1a, in an ASFA constructed in accordance with a preferred embodiment of the present invention, particles entrained within a stream of air emanating from an aerodynamic flow system such as ink jet aerosol generator 10, shown in FIG. 1b, are directed downward toward a detection volume 20. As noted above, detection volume 20 is defined by two nearly orthogonal, different-wavelength diode-laser trigger beams (trigger beams 1 and 2, emitting light at 635 and 670 nm, respectively), which are aimed and focused precisely to define an approximate 15-nm diameter focal volume position just upstream (about 50 micron) of the first focal plane of reflecting objective 30. As a particle from the aerodynamic flow system passes through the intersection of trigger beams 1 and 2 (defined as the trigger volume), light is scattered from the particle and is detected by photomultipliers (PMTs) 40 and 50. PMT 40 is equipped with a narrowband interference filer at 670 nm so that it only detects light scattered from trigger beam 1. Likewise, PMT 50 is equipped with a narrowband interference filer at 635 nm so that it will only detect scattered light from trigger beam 2. The intensity of the scattered light will be proportional to the size of the particle. To avoid detection of particles that are outside the size range of interest, the output signals from PMTs 40 and 50 are processed by a pair of single channel analyzers (SCA) 60 and 70 which operate as discriminators in a window mode. The PMT output pulses must exceed a preset lower voltage level and be less than a preset higher voltage level (set in the window mode) before the SCA will provide an output pulse. Thus, fluorescence spectra are measured only for particles falling within a preset size interval. The two SCA outputs are fed into a logic AND gate 80, which produces an output pulse only when the SCA output signals overlap. The output of AND gate 80 triggers Q-switched UV laser 90 to fire and also turns on intensified charge coupled device(ICCD) controller 95 which activates the ICCD camera 96 to record only when the laser 90 fires. Thus, particles not flowing through trigger volume 20, which would not be illuminated by the central portion of the beam from UV laser 90, and which are not in the focal region of reflecting objective 30, are ignored. The system is completed by spectrograph 97 with long pass filter 98, which disperses the fluorescence to ICCD camera 96 and ICCD controller 95. The output of ICCD controller 95 is fed to a computer 100 where data may be displayed, stored and analyzed. In particular, pattern recognition algorithms can be employed on computer 100 to detect and classify, or at least partially characterize natural indoor and outdoor aerosols.

Various modifications and alternatives are possible. For example, in one alternative embodiment, leakage of scattering from trigger beams 1 and 2 could be eliminated by signaling the diode lasers to turn off using the same signal from the logic circuit as is used to trigger the pulsed UV laser 90. Probe laser 90 is preferably a tightly focused pulsed UV laser triggerable on demand and of sufficiently high intensity or fluence to excite fluorescence in microparticles. In the prototype, Probe laser 90 was a Q-switched UV laser, either 266 nm, 4-th harmonic of a Nd:YAG laser, 30- or 70-ns pulse duration, 0.1 to 0.2 mJ per pulse (Spectra Physics models X-30 or Y-70), or 351 nm, 3rd harmonic of a Nd:YLF laser, 120 ns pulse duration, 1.65 mJ per pulse (Quantronix). The Q-switched laser was set to fire within approximately 3 microseconds of the trigger pulse (from the AND circuit), during which time the particle traveled (at a speed of about 10 m/s) about 30 micrometers. Various other probe lasers could be employed, depending on the type of particle and fluorescence to be detected.

The vertical displacement between the location where the particle is detected (trigger volume) and the location where the particle is probed (detection volume) can be compensated for by a small vertical displacement of the focal volume of trigger beams 1 and 2 from probe laser 90, which is focused at a focal plane of the reflecting objective. Alternatively, the displacement of these two volumes could be compensated for by a variable electronic delay, with the delay based on the speed at which particles are introduced into the focal volume.

In another preferred embodiment, multiple-wavelength excitation (e.g., one wavelength within the absorption band for tryptophan, and a longer wavelength for other biological molecules) could be used to better identify biological particles.

Reflecting objective 30 preferably has a large numerical aperture that can collect fluorescence from the emitting particle over a large solid angle, and focus it onto the slit of a spectrograph without chromatic aberration. In a preferred embodiment, reflective objective 30 (a so-called Schwartzchild reflecting objective) is manufactured by the Ealing Company and has numerical aperture 0.5 Alternatively, the sensitivity of the AFSA could be increased by adding a spherical reflector on the side opposite the Schwartzchild objective, or by replacing the Schwartzchild reflective objective 30 with a parabolic or ellipsoidal reflector. With this modification, particles would be excited to fluoresce when they traverse the focal point of the reflector. The parabolic reflector would collect the fluorescence, which would be focused onto the slit of spectrograph 97 as with the Schwartzchild reflecting objective.

In the prototype, ICCD camera 96 is manufactured by Princeton Instruments. ICCD camera 96 is placed at the exit port of the spectrograph 97 (an Acton model SP-150 with 300 grove/mm grating blazed at 500 nm, numerical aperture 0.125, input slit width 1 mm). The image intensifier of ICCD camera 96 acts as a fast shutter, opening when the targeted particle is illuminated by the UV laser. A long pass filter 98 is placed in front of spectrograph 97 to block elastically-scattered light and to pass the fluorescence. As an alternative to the ICCD, a multiple-channel photomultiplier tube (PMT), sample-and-hold, and multiplexer can be used. The multiple-channel PMT provides the advantages of comparable sensitivity, compactness, and lighter weight compared to the ICCD. A 32 channel system should provide sufficient spectral resolution to classify bioaerosol particles. This refinement will allow for more rapid sampling of aerosol particles, slower data rates, and more portability.

The capability of the present invention is demonstrated in FIGS. 2 and 3a and 3b. FIG. 2 shows the sensitivity and reliability of the AFSA detection system with *E. coli*. The overall fluorescence quantum efficiency of dry *E. coli* excited with 266-nm light may be about 3% of that of pure tryptophan (based on the fraction of the dry weight in tryptophan and tyrosine). The uniformity of the fluorescence spectra from single nominal 4 micron-diameter particles of dried *E. coli* is exhibited in the sequence of 10 consecutive spectra of nearly uniform particles in FIG. 2. The broad fluorescence peak at 350 nm is mainly from tryptophan, and the tail from 400 to 500 nm is attributed to fluorescence from residues of the nutrient growth material (which may have contributions from reduced nicotinamide compounds). The sharp peaks at 266 nm, 532 nm, 635 nm, and 670 nm are from leakage of the 266-nm beam, the 532-nm beam that generates the 266-nm light, and the two cw diode lasers, respectively. (In these spectra the peaks at 266 and 532 nm are larger than in some of the subsequent figures, probably because in this figure something nearby scattered more light toward the lens—the background is sensitive to the alignment and to the position of beam blocks.) The 635-nm and 670-nm peaks have been truncated for clarity of presentation. The spectra shown in FIG. 2 are similar from particle to particle and demonstrate that the system can capture, in real time, the fluorescence spectra of fairly low quantum-efficiency, micron-sized bioaerosols with a high SNR and good spectral resolution.

Unlike the uniform *E. coli* bacteria shown in FIG. 2, the biological particles of interest for field applications may be entrained with other aerosol particles that comprise the background. Average fluorescence spectra (which are the sum of the spectra for many aerosol particles) may yield little or no information about the few particles of interest. Hence, it is important for a Wieldable detector to be able to measure good-quality spectra from single particles as they are sampled from a complex mixture. This capability of the present invention is demonstrated in FIG. 3a, which shows 20 consecutive single-shot fluorescence spectra of particles generated from a sample collected from a chicken house. The sample was mixed with water and aerosolized using the IJAG. The average particle diameter was approximately 3 microns. Most of the fluorescence spectra are similar to the single-shot spectra labeled (a) in the inset to FIG. 3*b* (these have a broad emission from about 300 to 600 nm). The more smooth line in (a) overlapping the single-shot result shows the average spectrum of the 100 consecutive single shots. The spectra labeled (b) and (c) in FIG. 3*b* show the 4th and 48th fluorescence spectra from the series of 100 single shots. These are distinctly different from the other spectra. The 4th spectrum (curve c) has a band with two peaks located near 320 nm and a broader band that peaks around 450 nm. The 48th spectrum (curve b) has its strongest emission closer to 350 nm.

Chicken house dusts are complicated, with a large variety of microbes mixed in a background of organic, inorganic, and biological matter. In the sample measured here the total culturable microbial component is only 1% of the weight, and the culturable fungal species make up less than 0.006% of the weight. The dominant bacterial species are Staphylococcus aureus and Brevibacterium. The uniformity of the large; majority of the spectra in FIG. 3*a* suggests that the major fluorescing component of these particles is either soluble or is in the form of very small particulates so that the fluorophors are distributed somewhat uniformly in the suspension, used in the IJAG. The fact that the 4th and $48^{th}$ spectra exhibit much larger and spectrally distinct fluorescence suggests that some of the fluorescing material is not uniformly dispersed in the suspension. The present invention is able to differentiate these uncommon particles from the background. FIGS. 3*a* and 3*b* demonstrate the capability of the AFSA to detect rare particles that are mixed with a dominant concentration of background particles.

Although the invention has been described in detail above, the description is of preferred exemplary embodiments of the present invention. Many other variations and modifications can be made by one skilled in the art without departing from the spirit and scope of the invention as described in the following claims.

We claim:

1. An Aerosol Fluorescence Spectrum Analyzer comprising:

an optical element which transfers light from a particle detection region in a first focal plane to a second focal plane;

an aerodynamic flow system to move particles to and through the detection region;

a first trigger laser emitting a beam of wavelength $\lambda_1$ and focused in a trigger region through which particles flow on their way to the detection region;

a second trigger laser emitting a beam of wavelength $\lambda_2$ aimed in a direction approximately orthogonal to the direction of the first trigger laser and focused on the trigger region, the trigger region being defined by the intersection of the first and second trigger laser beams;

a first wavelength-selective photodetector sensitive to light scattered from the trigger region and emitting an output signal in response to light of wavelength $\lambda_1$;

a second wavelength-selective photodetector sensitive to light scattered from the trigger region and emitting an output signal in response to light of wavelength $\lambda_2$;

a pulsed probe laser which emits a pulse of light centered on a particle detection volume triggered by the logically ANDed output signals of the first and second wavelength-selective photodetectors to emit a pulse of light substantially in the first focal plane and downstream of the trigger region;

a spectral dispersing element positioned in the second focal plane; and a photosensor optically connected to the spectral dispersing element, triggered by the logically ANDed outputs of the first and second wavelength-selective photodetectors.

2. An Aerosol Fluorescence Spectrum Analyzer according to claim 1 wherein the photosensor comprises a CCD array.

3. An Aerosol Fluorescence Spectrum Analyzer according to claim 1 wherein the photosensor comprises a multiple anode photomultiplier tube.

4. An Aerosol Fluorescence Spectrum Analyzer according to claim 1 wherein the optical element comprises a lens.

5. An Aerosol Fluorescence Spectrum Analyzer according to claim 1 wherein the optical element comprises a reflective objective.

6. An Aerosol Fluorescence Spectrum Analyzer according to claim 5 wherein the reflective objective comprises a Schwartzchild optical element.

7. An Aerosol Fluorescence Spectrum Analyzer according to claim 5 wherein the reflective objective comprises a parabolic optical element.

8. An Aerosol Fluorescence Spectrum Analyzer according to claim 5 wherein the reflective objective comprises an ellipsoidal objective.

9. An Aerosol Fluorescence Spectrum Analyzer according to claim 1 wherein the optical element comprises both a reflecting objective and a spherical reflector positioned opposite the reflecting objective.

10. An Aerosol Fluorescence Spectrum Analyzer according to claim 1 wherein the pulsed laser is Q-switched.

11. An Aerosol Fluorescence Spectrum Analyzer according to claim 1 wherein the pulsed laser emits light in the UV range.

12. An Aerosol Fluorescence Spectrum Analyzer according to claim 1 wherein the first and second wavelength selective photodetectors comprise single channel analyzers operating in a window mode.

13. An Aerosol Fluorescence Spectrum Analyzer according to claim 1 wherein the aerodynamic flow system includes means to control the direction and speed of the particle.

14. An Aerosol Fluorescence Spectrum Analyzer according to claim 1 wherein at least one of the wavelength-selective photodetectors is responsive to light of a predetermined range of intensities.

15. An Aerosol Fluorescence Spectrum Analyzer comprising:

triggerable pulsed laser means for fluorescence probing of a particle;

optical means for collecting fluorescence emitted from the particle in a detection volume and for focusing it in a detection region;

first triggering laser means for directing and focusing a beam of light of wavelength $\lambda_1$ in a trigger volume substantially adjacent to the detection volume;

second triggering laser means for directing a beam of light of wavelength $\lambda_2$ in the trigger volume, in a direction approximately orthogonal to the direction of the beam emitted from the first triggering laser means;

first sensor means for providing an output signal upon detecting light of wavelength $\lambda_1$ scattered from a particle in the trigger volume;

second sensor means for providing an output signal upon detecting light of wavelength $\lambda_2$ scattered from a particle in the trigger volume;

spectral detector means gated by ANDed outputs of the first and second sensor means for detecting fluorescence emitted from a particle and focused by the optical means while the triggerable pulsed laser means is in the "on" state.

16. An Aerosol Fluorescence Spectrum Analyzer according to claim 15 wherein at least one of the sensor means is responsive to light of a predetermined range of intensities.

17. A method for fluorescence probing particles flowing in a fluid, comprising:

defining a trigger volume in the fluid by intersecting a plurality of substantially orthogonally aimed trigger laser beams, each of a different wavelength;

detecting light scattered from the vicinity of the trigger volume by a plurality of particle detectors each sensitive to a wavelength corresponding to the wavelength of a trigger laser beam;

probing the particles with a pulsed laser triggered by the particle detectors;

collecting fluorescence emitted from the particle in a detection volume and focusing it in a detection region;

detecting the fluorescence focused in the detection region.

18. A method for fluorescence probing particles flowing in a fluid according to claim 17 further comprising detecting light scattered from the vicinity of the trigger volume by a plurality of particle detectors each sensitive to a wavelength corresponding to the wavelength of a trigger laser beam and responsive to a predetermined range of intensities.

* * * * *